(12) United States Patent
Seidman

(10) Patent No.: US 8,014,870 B2
(45) Date of Patent: Sep. 6, 2011

(54) METHOD AND APPARATUS FOR THE TREATMENT OF TINNITUS

(76) Inventor: Michael D. Seidman, West Bloomfield, MI (US)

( * ) Notice: Subject to any disclaimer, the term of this patent is extended or adjusted under 35 U.S.C. 154(b) by 461 days.

(21) Appl. No.: 11/201,454

(22) Filed: Aug. 11, 2005

(65) Prior Publication Data
US 2006/0036297 A1    Feb. 16, 2006

Related U.S. Application Data

(60) Provisional application No. 60/600,671, filed on Aug. 11, 2004.

(51) Int. Cl.
*A61N 1/36* (2006.01)
*A61B 5/055* (2006.01)
(52) U.S. Cl. ............... 607/55; 600/411; 600/544
(58) Field of Classification Search ........... 607/55–57, 607/73, 116, 117; 600/378, 407, 409–411, 600/417–418, 544, 559
See application file for complete search history.

(56) References Cited

U.S. PATENT DOCUMENTS

| | | | | |
|---|---|---|---|---|
| 5,496,369 | A | 3/1996 | Howard, III | 623/10 |
| 5,697,975 | A | 12/1997 | Howard, III et al. | 623/10 |
| 6,430,443 | B1 * | 8/2002 | Karell | 607/55 |
| 6,456,886 | B1 | 9/2002 | Howard, III et al. | 607/55 |
| 6,631,295 | B2 | 10/2003 | Rubinstein et al. | 607/55 |
| 6,682,472 | B1 | 1/2004 | Davis | 600/25 |
| 6,925,332 | B2 * | 8/2005 | Franck | 607/57 |
| 2003/0114728 | A1 * | 6/2003 | Choy | 600/28 |
| 2003/0135248 | A1 * | 7/2003 | Stypulkowski | 607/73 |
| 2004/0138550 | A1 * | 7/2004 | Hartlep et al. | 600/407 |
| 2005/0070971 | A1 * | 3/2005 | Fowler et al. | 607/45 |
| 2005/0159792 | A1 * | 7/2005 | Ridder | 607/57 |

OTHER PUBLICATIONS

Henry et al., Comparison of two computer-automated procedures for tinnitus pitch matching, Journal of Rehabilitation Research and Development, 2001, pp. 557-566, vol. 38, No. 5.*
Cohen, Leonardo G. et al., Functional relevance of cross-modal plasticity in blind humans, Nature, Sep. 11, 1997, vol. 389 (6647), pp. 180-183.
Barkley, Gregory L. et al., MEG and EEG in Epilepsy, Journal of Clinical Neurophysiology, (2003), vol. 20 (3), pp. 163-178.
Moller, Margareta B. et al., Vascular Decompression Surgery for Severe Tinnitus: Selection Criteria and Results, Laryngoscope, Apr. 1993, vol. 103, pp. 421-427.

(Continued)

*Primary Examiner* — Carl H Layno
*Assistant Examiner* — Jessica Sarcione
(74) *Attorney, Agent, or Firm* — Gifford, Krass, Sprinkle, Anderson & Citkowski, P.C.

(57) ABSTRACT

A method and apparatus for electrically stimulating the brain to alleviate tinnitus. In one aspect of the invention the areas of the brain to which stimulation is applied are determined by a procedure which first involves analysis of the patient to determine the nature of the sound perceived by the patient to produce tinnitus. These sound frequencies are then provided to the patient while imaging studies are made of the patient's brain. These studies may include magnetoencephalography (MEG) and/or functional magnetic resonance imaging (fMRI). These studies are then analyzed to determine the locus of the tinnitus, and one or more electrodes are placed at the indicated region in the patient's brain and a stimulation device for outputting a varying control pattern of electrical signals to the electrodes is also implanted.

6 Claims, 1 Drawing Sheet

OTHER PUBLICATIONS

Hirsch, Joy et al., Illusory contours activate specific regions in human visual cortex: Evidence from functional magnetic resonance imaging, Proc. Natl. Acad. Sci., Jul. 1995, vol. 92, pp. 6469-6473.

Mirz, Frank, Cortical Networks Subserving the Perception of Tinnitus—a PET Study, Acta Otolaryngol, (2000), Suppl 543, pp. 241-243.

Rubinstein, Jay T. et al., Electrical Suppression of Tinnitus with High-Rate Pulse Trains, Otology & Neurotology, (2003), vol. 24, No. 3, pp. 478-485.

Dostrovsky, J. O. et al., Microstimulation—Induced Inhibition of Neuronal Firing in human Globus Pallidus, Rapid Communication, (2000), pp. 570-574.

Boraud, Thomas, High frequency stimulation of the internal Globus Pallidus (GPi) simultaneously improves parkinsonian symptoms and reduces the firing frequency of GPi neurons in the MPTP—treated monkey, Neuroscience Letters, (1996), vol. 215, pp. 17-20.

Chen, R. et al., Depression of motor cortex excitability by low-frequency transcranial magnetic stimulation, Neurology, May 1997, vol. 48(5), pp. 1398-1403.

Boroojerdi, B. et al., Reduction of human visual cortex excitability using 1-Hz transcranial magnetic stimulation, Neurology, Apr. 11, 2000, vol. 54(7), pp. 1529-1531.

Ito, Juichi et al., Suppression of Tinnitus by Cochlear Implantation, American Journal of Otolaryngology, (1994), vol. 15, No. 2, pp. 145-148.

Brookes, Gerald B. et al., Vascular-Decompression Surgery for Severe Tinnitus, The American Journal of Otology, (1996), vol. 17, No. 4, pp. 569-576.

Inghilleri, M. et al., Effects of transcranial magnetic stimulation on the H reflex and F wave in the hand muscles, Clinical Neurophysiology, (2003), vol. 114, pp. 1096-1101.

Kim, Seong-Gi et al., Functional Magnetic Resonance Imaging of Motor Cortex: Hemispheric Asymmetry and Handedness, Science, Jul. 30, 1993, vol. 261(5121), pp. 615-617.

Flor, H. et al., Phantom-limb pain as a perceptual correlate of cortical reorganization following arm amputation, Nature, Jun. 8, 1995, vol. 375(6531), pp. 482-484.

Tellier, A. L. et al., Charge Syndrome: Report of 47 Cases and Review, American Journal of Medical Genetics, (1998), vol. 76, pp. 402-409.

Claussen, C. F. et al., On The Functional State of Central Vestibular Structures in Monoaural Symptomatic Tinnitus Patients (BEAM-VbEP Study), International Tinnitus Journal, (1995), vol. 1, No. 1, pp. 5-12.

Soussi, Thierry et al., Effects of Electrical Brainstem Stimulation on Tinnitus, Acta Otolaryngol (Stockh), (1994), vol. 114, pp. 135-140.

Hesse, G. et al., Ergebnisse stationarer Therapie bei Patienten mit chronisch komplexem Tinnitus, Laryngo-Rhino-Otol, (2001), vol. 80, pp. 503-508.

Jastreboff, Pawel J. et al., Tinnitus Retraining Therapy for patients with tinnitus and decreased sound tolerance, Otolaryngol Clin N Am, (2003), vol. 36, pp. 321-336.

Steenerson, Ronald L. et al., Treatment of tinnitus with electrical stimulation, Otolaryngology—Head and Neck Surgery, Nov. 1999, pp. 511-513, vol. 121, Atlanta, GA.

Plewnia MD, Christian et al., Transient Suppression of Tinnitus by Transcranial Magnetic Stimulation, Annals of Neurology, 2003, pp. 263-266, vol. 53, No. 2, Wiley-Liss, Inc.

Belliveau et al., Functional Mapping of the Human Visual Cortex by Magnetic Resonance Imaging, Science, Nov. 1991, pp. 716-718, vol. 254.

Knecht et al., Changing Cortical Excitability with Low-Frequency Transcranial Magnetic Stimulation Can Induce Sustained Disruption of Tactile Perception, Biol Psychiatry, 2003, pp. 175-179, vol. 53, Society of Biological Psychiatry.

Plewnia et al., Disinhibition of the contralateral motor cortex by low-frequency rTMS, NeuroReport, Mar. 24, 2003, pp. 609-612, vol. 14, No. 4, Lippincott Williams & Wilkins.

Ebersole, Magnetoencephalography/Magnetic Source Imaging in the Assessment of Patients with Epilepsy, Epilepsia, 1197, pp. S1-S5, vol. 38 (Suppl. 4), Lippincott-Raven Publishers, Philadelphia.

Hoffman MD et al., Slow Transcranial Magnetic Stimulation, Long-Term Depotentiation, and Brain Hyperexcitability Disorders, Am J Psychiatry, Jul. 2002, pp. 1093-1102, vol. 159.

Bowyer et al., Magnetoencephalographic Validation Parameters for Clinical Evaluation of Interictal Epileptic Activity, Journal of Clinical Neurophysiology, 2003, pp. 87-93, vol. 20 (2), Lippincott Williams & Wilkins, Inc., Philadelphia.

* cited by examiner

METHOD AND APPARATUS FOR THE TREATMENT OF TINNITUS

RELATED APPLICATION

This application claims priority of U.S. Provisional Patent Application Ser. No. 60/600,671 filed Aug. 11, 2004, which is incorporated herein by reference.

FIELD OF THE INVENTION

The present invention relates to methods and apparatus for the treatment of tinnitus and more particularly to an improved method of treatment of tinnitus by electrical stimulation of the brain.

BACKGROUND OF THE INVENTION

Tinnitus is any sound perceived to be coming from the head or ears without an external sound source. Tinnitus is a distressing symptom affecting up to 30% of the population, with 2-4% severely debilitated. Any lesion along the tonotopically organized auditory tract, influencing its normal function, can generate tinnitus. The layout of the auditory tract is genetically determined but its tonotopy arises in response to sensory input during critical periods of early development. Any alteration of the normal sensory input in the fully developed auditory system leads to a reorganization of the entire auditory tract starting peripherally and ending cortically. This reorganization occurs in two phases and it follows the same Darwinian rules that apply for the developmental organization of the auditory system.

After frequency selective monaural cochlear or auditory tract lesions, the tonotopic map in the brainstem nuclei and auditory cortex can reorganize within one to three hours such that cortical neurons deprived of their usual afferent input become supersensitive and then respond to tone frequencies adjacent to the frequency range damaged by the lesion (lesion-edge frequencies). Tinnitus most probably arises when auditory cortical cells are processing auditory input for which they are not predestined. The tonotopic maps for input from each ear can be independently modified, so that a lesion in one ear results in an altered cortical map contralaterally, while the tonotopic map of the intact cochlea remains unaltered. This produces a tonotopic mismatch that can be visualised using magnetic source imaging. Furthermore there is a high positive association between subjective tinnitus strength and the amount of shift of the tinnitus frequency in the auditory cortex. This is similar to the amount of reorganization of the somatosensory cortex and the amount of phantom limb pain.

Since little is known on the pathophysiology of tinnitus, a closer look at the pathophysiology of phantom pain can facilitate a better understanding of tinnitus. The "gate control" theory proposes that a "pain gate" exists in the dorsal horns in the spinal cord. This gate is either open or closed for transmission of painful stimuli to the brain. Whether the gate is open or closed depends on a balance of small (c-fibers) and large fibers ($A_\alpha$ and $A_\beta$). The gate would open, thus giving rise to the subjective feeling of pain, in response to an excess of small fiber activity and close in response to predominantly large fiber activity. These large fibers have a lower threshold for depolarization to an electrical stimulus and can thus be selectively recruited. Therefore electrical treatment stimulating these large fibers selectively can change the balance between small and large fiber afferents, thus closing the pain gate. Based on this principle, spinal cord stimulation is used ever more frequently for patients with phantom pain. As the amount of phantom pain is strongly correlated with the amount of reorganization in the somatosensory cortex, we would expect this reorganization to reverse in patients successfully treated with spinal cord stimulation for phantom pain. This reorganization is exactly what has been observed in patients with neuropathic pain who become pain free after spinal cord stimulation as demonstrated by magnetoencephalography (MEG).

Tinnitus can be treated with electrical stimulation, transcutaneously, at the promontory or with a cochlear implant. Results vary but the more central the stimulation, the more reduction in tinnitus can be observed.

Based on the anatomy (tonotopic organization of dorsal cochlear nucleus and cortex), the pathophysiology (gate control hypothesis and auditory tract reorganization) and the clinical results of electrical stimulation (cochlear implants), it can be theoretically hypothesized that brainstem and auditory cortex stimulation may have an effect on tinnitus relief in patients with or without significant hearing loss. Stimulating selectively, the frequency of hearing loss or the tinnitus level should prevent reorganization at the brainstem and at the auditory tract all the way up to the auditory cortex, thus preventing or treating the tinnitus as long as reorganization has not yet reached the second phase of irreversible cortical, thalamocortical and corticothalamic connection formation. This implies that tinnitus should be treated as soon as possible, preferably within a few years of onset. This does not mean that this procedure will not work for patients who have had tinnitus for longer durations, but it is possible that treatment may be less effective. Indirect arguments for not delaying treatment for tinnitus come from results of microvascular decompressions performed in the treatment of neurovascular compression tinnitus. There is a clear correlation between the duration of tinnitus and the success rate of the surgical decompression.

In one study the effects of electrical brainstem stimulation on tinnitus were analyzed in bilaterally deaf NF-2 patients with brainstem implants placed for auditory stimulation. The tinnitus was improved in eight of ten patients, suggesting prospective studies with brainstem stimulation are waranted.

In phantom pain, motor cortex stimulation is used as a treatment option. Similarly, auditory cortex stimulation may help relieve tinnitus. Its working mechanism seems to rely on cortico-thalamic connections, and not on cortical neurons or somatosensory neurons as demonstrated by PET studies. Thus stimulating the auditory cortex, lateral lemniscus, the inferior olive, medial geniculate body, dorsal cochlear nucleus, the cochlear nucleus and the superior olive either alone or separately could activate cortico-thalamic connections resulting in thalamic reorganization, with relief of tinnitus as a result.

There is currently no cure for tinnitus. There are several modalities that may be of benefit to some patients. These include: vitamin and herbal therapies, masking techniques, pharmacologic strategies (focused primarily on anxiolytics and antidepressants), tinnitus retraining therapy, and complementary and integrative therapies (i.e., acupuncture, hypnotherapy, biofeedback).

U.S. Pat. No. 5,697,975 teaches that electrical stimulation to the brain, specifically the auditory cortex will eliminate tinnitus. This is true only in part: The tinnitus will likely be decreased for a short period of time i.e., 1-4 days. Then the brain reorganizes and the tinnitus returns. Thus, there is a need for such a tinnitus treatment.

Moreover, in treatment of tinnitus by electrical stimulation of the brain there is a need for improving methods of localizing the stimulation areas within the brain.

SUMMARY OF THE INVENTION

The present invention is accordingly directed toward an improved method and apparatus for electrically stimulating the brain to alleviate tinnitus. In one aspect of the invention the areas of the brain to which stimulation is applied would be determined by a procedure which first involves analysis of the patient to determine the nature of the sound perceived by the patient to produce tinnitus. Then these sound frequencies will be provided to the patient while imaging studies are made of the patient's brain. These studies may include magnetoencephalography (MEG) and/or functional magnetic resonance imaging (fMRI). MEG is a non-evasive imaging technique that can be used to image the functional activity of the cortex, while fMRI is based on the increase in blood flow to the local vasculature that accompanies neural activity in the brain. These studies are then analyzed to determine the locus of the tinnitus, and one or more electrodes are placed at the indication region in the patient's brain and a stimulation device for outputting electrical signals to the electrodes is also implanted.

In another aspect of the invention the electrical signals provided by the generator to the electrodes vary over time, rather than being a continuous, static pattern. It has been determined that the application of a static stimulation pattern will improve tinnitus for a few days, but the brain becomes inured to that pattern and varying the pattern over time prevents such acclimation and the subsequent return of tinnitus.

BRIEF DESCRIPTION OF THE DRAWING

Other objects, advantages and applications of the present invention will be made apparent by the following detailed description of the invention wherein the description makes reference to the accompanying drawing in which.

DETAILED DESCRIPTION OF THE PREFERRED EMBODIMENT

Figure 1:
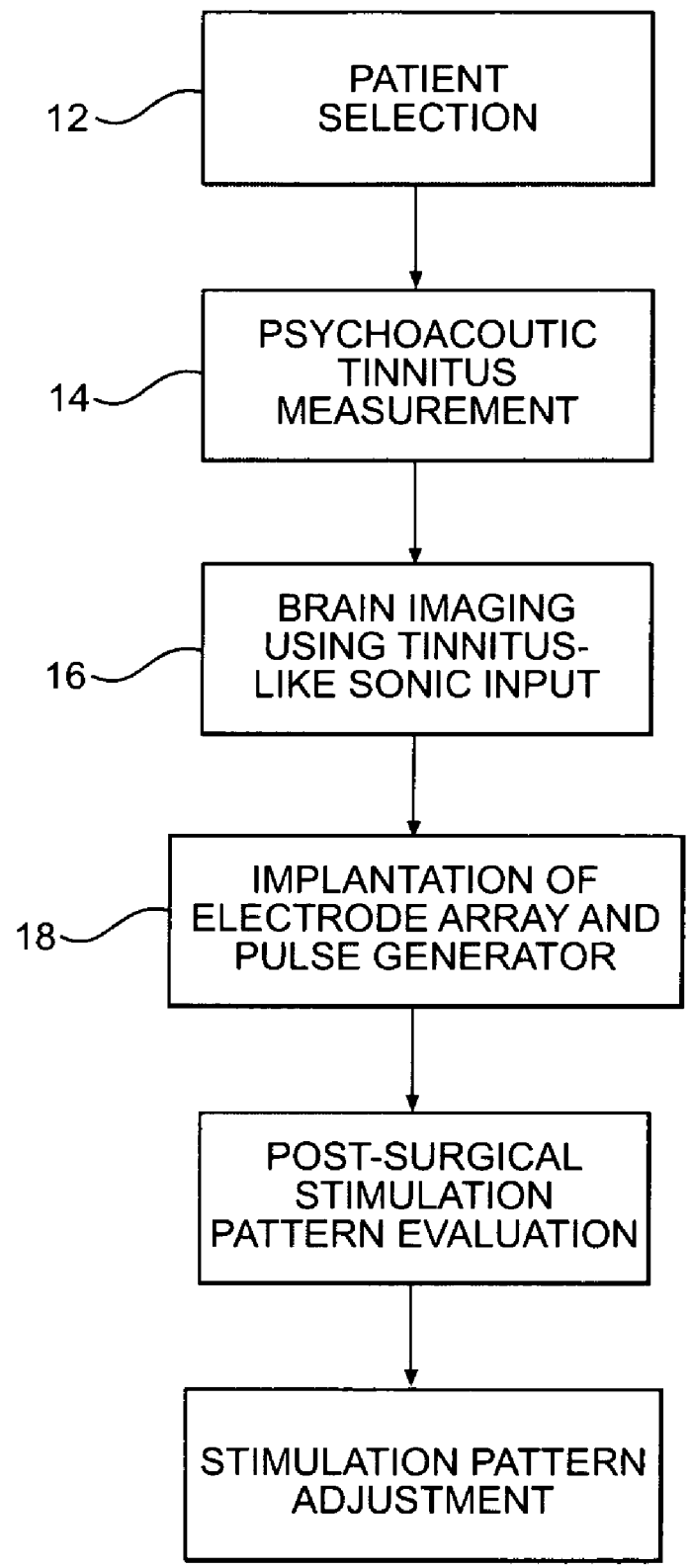
FIG. 1 is a flowchart setting forth the sequence of steps employed in the method of the present invention.

FIG. 1 broadly outlines the steps and method of the present invention. The first step, indicated at 12, is patient selection; that is, identifying a patient who suffers from subjective tinnitus and whose problem has not been relieved by a course of conservative, non-surgical tinnitus therapy. The patient is initially selected on the basis of unilateral or bilateral severe unremitting tinnitus. These therapies include dietary modification; elimination of caffeine, alcohol, simple sugars and salts; trial of medications and/or herbal therapies; and masking or tinnitus retraining therapy. The patient will have a physical examination and the history will be taken as well as a hearing evaluation using comprehensive audiometry.

The next step, generally indicated at 14 on the flowchart of FIG. 1, involves psychoacoustic tinnitus measurement and mapping. Mapping involves determining the precise sound amplitude and pitch that most closely describes the patient's actual tinnitus.

In one embodiment of mapping, the patient will be placed in a sound-treated booth and insert phones will be placed bilaterally. Measurements will begin with the ear that has been determined worse by previous tinnitus questionnaires and patient case history if bilateral tinnitus is present.

Loudness Measures

Loudness measures will be determined across frequencies so that the pitch measures are not influenced by unequal loudness presentations.

1. Patients will be asked to determine a loudness match, in dB HL, across 1000, 2000, 3000, 4000, 6000, 8000, and 12,000 Hz (if applicable to patient's loss).

2. A continuous tone at a given frequency will be presented to the contralateral ear below threshold and raised by the examiner in 1 dB steps at a rate of 1 dB/2 seconds until a match is achieved.

3. Once indicated that the contralateral tone is equal in loudness, the level will be recorded.

Pitch Matching

1. Pitch matching will be performed using a two-alternative forced-choice procedure. Tonal intensity levels will be the previously determined levels during the loudness match and presented contralaterally.

2. Patients will be asked to determine whether f1 or f2 is closer to the pitch of their tinnitus.

3. Presentations of the discrete pure tones will start at 1000 Hz and increase in frequency until the choices exceed the approximate pitch level (this will be determined by the patient beginning to choose f1 rather than f2).

4. Once an estimate of the pitch is determined, the two-alternative forced-choice procedure will be performed with the 1-2 pitches surrounding the approximate frequency match.

5. Tones an octave away from the chosen tone will also be given as choices to rule out octave confusion.

6. Seven choices of the pitch will be made in an attempt to increase reliability.

7. The procedure will also be repeated ipsilaterally to ensure that binaural diplacusis was not a factor in the match.

8. A new hearing threshold for the matched pitch will be obtained using a 1 dB step to better determine the sensation level (matched loudness dB level minus the audiological threshold).

9. An ascending approach beginning at −10 dB (previously established threshold, using the same bracketing procedure for the former threshold) will be used.

10. A repeat of the loudness match will be made using the pitch-matched frequency.

11. A continuous tone presented at 1 dB/2 seconds will be presented below threshold in the chosen ear (contralateral or ipsilateral to the tinnitus) and increased until the patient indicates that the tone is equivalent in loudness to the tinnitus.

12. Three matches will be obtained and the final match recorded in dB Sensation Level (SL) (the chosen loudness level minus the threshold).

Minimum Masking Levels

1. White noise will be delivered at −10 dB HL and the patient will indicate when it is audible.

2. The level will be lowered below threshold (or −10 dB HL) and raised until the patient indicates that the white noise is masking the tinnitus.

3. Presentations will be made ipsilaterally and bilaterally, if necessary.

Residual Inhibition

1. Residual inhibition will be measured by presenting the white noise 10 dB above the minimum masking level previously determined.

2. The white noise will be presented for 60 seconds ipsilaterally or bilaterally.

3. The patient will indicate by raising his/her hand when the tinnitus starts to return, and then putting their hand back down when it is back to its original loudness level.

Loudness Discomfort Levels (LDLs)

1. Loudness discomfort levels (LDLs) will be measured by presenting the tone at a comfortable level and then increasing the level in discrete 5 dB steps presented at 2-3 second durations, for 500, 1000, 2000, 3000, 4000, 6000, and 8000 Hz.

2. The patient will be instructed that it is a measure of sound tolerance and that we need to allow as much of an increase in loudness as possible before stopping.

3. However, the patient will indicate if the sound becomes uncomfortable and measures will be stopped immediately.

4. All frequencies will be tested twice and the second level will be recorded.

The patient will then undergo brain imaging using tinnitus-like sonic inputs which simulate the sonic stimuli that the patient reported as emulating the tinnitus symptoms, during the measurements of block 14. These brain imaging studies are generally indicated at 16 in FIG. 1. While a variety of non-evasive brain imaging techniques might be employed in connection with the present invention, including computed tomography or magnetic resonance imaging, which both provide structural/anatomical information, the present invention preferably employs magnetoencephalography (MEG) and/or functional MRI (fMRI) and most preferably a combination of the two.

Magnetoencephalography (MEG) is a noninvasive imaging technique that can be used to image the functional activity of the cortex. MEG analysis of simple primary cortical evoked responses is performed using the single equivalent current dipole (ECD) technique. This method is used to determine the location of compact cortical sources involved in brain activity and subsequently map these locations on MRI images of the brain. This methodology works well for stationary, non-distributed sources such as early cortical latencies in auditory evoked response data.

Magnetoencephalography (MEG) is a completely noninvasive and non-hazardous technology for functional brain mapping. MEG provides spatial discrimination of 2-5 mm and an excellent temporal resolution on the order of 1 ms. It localizes and characterizes the electrical activity of the central nervous system by measuring the associated magnetic fields emanating from the brain. Every current generates a magnetic field according to the right hand rule of physics. This same principle is applied in the nervous system whereby the longitudinal neuronal current flow generates an associated magnetic field. MEG measures the intercellular currents of the neurons in the brain giving direct information on brain activity, spontaneously or to a given stimulus. Measurement preparation and collection times are relatively short and can be performed by a technician. Magnetoencephalography (MEG) is currently used clinically for pre-surgical localization of epileptic tissue, based on signals from interictal spikes, using single equivalent current dipole (ECD) modeling.

MEG is a functional imaging capability complementary to the anatomical imaging capabilities of MRI and CT. That is, whereas MRI and CT are capable of imaging anatomy, MEG is able to image neurological function. MEG measures the activity of the brain in real time. The brain can be observed "in action" rather than just viewing a still MR image. MEG data can be used to identify both normal and abnormal functions of brain structures, which are anatomically seen in the static MRI scans. The two modalities can then be fused into a composite image of function and anatomy. As a result, the combination of MEG and MRI techniques has considerable clinical use.

MEG combines many of the advantages of various other new functional imaging modalities, such as Positron Emission Tomography (PET) and functional MRI (fMRI), which are weakly invasive and measure signals caused by changes of blood flow. In PET radioactive marker substances are injected into the subject's bloodstream, and, in fMRI, the patient is exposed to a high static magnetic field and a small alternating radiofrequency field, with no health hazards reported. The temporal resolution of PET is tens of seconds, and although fMRI can be collected at 50 to 100 ms intervals, the intrinsic inertia of changes in blood flow limits the temporal resolution of fMRI to 1 s. However, MEG's temporal resolution of 1 ms is far superior than the others, while having an equivalent spatial resolution.

fMRI is based on the increase in blood flow to the local vasculature that accompanies neural activity in the brain. This results in a corresponding local reduction in deoxyhemoglobin because the increase in blood flow occurs without an increase of similar magnitude in oxygen extraction. Since deoxyhemoglobin is paramagnetic, it alters the $T2^*$ weighted magnetic resonance image signal. Thus, deoxyhemoglobin is sometimes referred to as an endogenous contrast enhancing agent, and serves as the source of the signal for fMRI. Using an appropriate imaging sequence, human cortical functions can be observed without the use of exogenous contrast enhancing agents on a clinical strength (1.5 T) scanner. Functional activity of the brain determined from the magnetic resonance signal has confirmed known anatomically distinct processing areas in the visual cortex, the motor cortex, and Broca's area of speech and language-related activities. Further, a rapidly emerging body of literature documents corresponds to findings between fMRI and conventional electrophysiological techniques to localize specific functions of the human brain. Consequently, the number of medical and research centers with fMRI capabilities and investigational programs continues to escalate.

The main advantages to fMRI as a technique to image brain activity related to a specific task or sensory process include (1) the signal does not require injections of radioactive isotopes; (2) the total scan time required can be very short, i.e., on the order of 1.5 to 2.0 min per run (depending on the paradigm); and (3) the in-plane resolution of the functional image is generally about 1.5×1.5 mm, although resolutions less than 1 mm are possible. To put these advantages in perspective, functional images obtained by the earlier method of PET require injections of radioactive isotopes, multiple acquisitions, and, therefore, extended imaging times. Further, the expected resolution of PET images is much larger than the usual fMRI pixel size. Additionally, PET usually requires that multiple individual brain images are combined in order to obtain a reliable signal. Consequently, information on a single patient is compromised and limited to a finite number of imaging sessions. Although these limitations may serve many neuroscience applications, they are not optimally suitable to assist in a neurosurgical or treatment plan for a specific individual.

fMRI can be used to indirectly measure the amount of neural activity in a particular structure in the central nervous system. The technique measures the aggregate oxygen consumption of neurons within the block of tissue (generally 3×3×6 mm) that composes a three-dimensional voxel. Varying levels of oxygen in the tissue results in a change in the absolute level of the signal obtained from the experiment. The fMRI experiments are conducted using a standard clinical MRI system that has been programmed to collect quick lower-resolution images in rapid succession. The large magnet undergoes a conformational change in order to select the plane of interest. In doing so, the scanner creates a loud sound that is typically a harmonic complex centered around 1000 Hz at a level of about 115 dB SPL for a 1.5 Tesla magnet. When performing experiments involving the auditory system, special noise-reduction protocols must be used to decrease the reception of this contaminant noise by the subject. This noise reduction is accomplished by a variety of measures, including passive measures of shielding the subject from the external sound (through noise-reduction headphones and foam surrounding the head) and experimental measures to decrease the rate of image collection and/or number of slices imaged.

The sequence of tests used in the preferred embodiment of the invention is a pair of MEG tests and a pair of fMRI tests as set forth below.

MEG Test 1

Auditory Evoked Cortical Magnetic Fields (AECMFs) will be recorded using 1000 Hz tones generated outside the shielded room and delivered monaurally without masking at 40 dB HL to an earpiece using 3 meter long hollow tubing. The tone burst will consist of a 250 ms duration tone with a 15 ms rise/fall time. The tone burst will be repeated 150 times, delivered once every 2 seconds. One hundred and fifty epochs will be averaged with a 200 ms pre-stimulus baseline and 1800 ms post-stimulus time. The low pass filter will be 0.1 Hz, the high pass filter will be 100 Hz, and the sampling rate will be 508.63 Hz. Each ear will be tested separately. Two trials will be performed for each ear. This test is made up of four trials lasting ~5 minutes each.

MEG Test 2

AECMFs will be recorded using a 40 Hz tone or a tone with matching pitch to their tinnitus. The stimulus will be delivered as described above. The burst will consist of a 250 ms duration with a 15 ms rise/fall time and presented 150 times once every 2 seconds. Analysis will be carried out as described above.

Analysis of MEG Data

MRIs will be performed as described below and used to co-register to the MEG data for precise localization of the auditory cortex of interest. Images will be converted to volumetric MRI data with isotropic pixel dimensions using STA/R software (4D Neuroimaging, San Diego Calif.). In addition, the STA/R software will be used to co-register the MRI row, column and slice coordinates to the subject's MEG x, y, z coordinate system established during data acquisition. The techniques for co-registration of MEG and MRI are well established and used in all of our clinical MEG studies.

MEG data will be digitally filtered 1-50 Hz. An epoch data duration of 0-400 ms will be used for analysis. Data analysis will be carried out utilizing Single Equivalent Current dipole (ECD) source analysis to determine latency, location and amplitude of the cortical responses of each individual during each auditory task performance. Localizations will be mapped on to each subject's MRI image.

The AECMF responses will be visually inspected and the major peak latency corresponding to p100 will be identified. The single ECD fit for each peak in the right and the left hemisphere will be calculated. The dipole selection criteria includes a correlation coefficient and goodness of fit of 0.98 or better, an RMS (in fT) of at least twice the signal strength (in nanoAmp-Meters) of the dipole moment (Q), and a confidence volume preferably less than 1 cm$^3$.

fMRI Study fMRI scans allow for a precise localization of the anatomical landmarks and cortical activation area arising from the auditory and visual tasks performed in MEG and fMRI. These MRI scans may be performed on a clinical GE 3.0 Tesla, 1 meter bore whole body magnet. The MRI scan parameter will include the entire skin surface of the head. Standard anatomic scans will be acquired lasting about 10 minutes before experimental scans. The anatomic scan will include: (1) a 3 planes localizer using a fast gradient echo sequence (TE/TR 1.7/32 msec, imaging matrix 256×128); and (2) a volumetric scan (3D inversion recovery spoiled gradient echo sequence with TE/TI/TR 4.5/300/10.4 msec, imaging matrix 256×256×200). The subject will change into a hospital gown and remove all metal articles from his/her body. Compressible ear plugs will be given to attenuate the sound generated by the fMRI machine. The subject will then lie comfortably on the bed that will be slowly moved into the MRI. The subject will be placed in the MRI scanner. The subject will be asked to avoid excessive eye and body movements during data collection. The subject will be monitored by two-way audio speaker system during the time he/she is in the MRI scanner. This study will take approximately 25 minutes to perform.

fMRI Test 1

Auditory Evoked Responses (AERs) will be recorded using the same paradigm as described in MEG test 1. A 1000 Hz tone will be generated outside the shielded room and delivered monaurally without masking at 40 dB HL to an earpiece using a 3 meter long hollow tube. The tone burst will consist of a 250 ms duration tone with a 15 ms rise/fall time. The tone burst will be repeated 150 times, delivered once every 2 seconds. Activation will be measured during auditory tones utilizing a block design of alternating 8.8 seconds of activation (tone on) and 8.8 seconds of non-activation (tone off). This test will consist of two trials lasting ~3 minutes each. Each ear will be tested separately. Two trials will be performed for each ear. This test is made up of four trials lasting ~5 minutes each.

fMRI Test 2

AERs will be recorded using a 40 Hz tone or a tone that matches their tinnitus. The stimulus will be delivered as described above. The burst will consist of a 250 ms duration with a 15 ms rise/fall time and presented 150 times once every 2 seconds. Activation will be measured during auditory tones utilizing a block design of alternating 8.8 seconds of activation (tone on) and 8.8 seconds of non-activation (tone off). This test will consist of two trials lasting ~3-minutes each. Each ear will be tested separately. Two trials will be performed for each ear. This test is made up of four trials lasting ~5 minutes each.

fMRI Analysis

Statistical parametric mapping (SPM) will be used to determine the location and significance of neuronal activation from raw fMRI data. Each fMRI sequence will be pre-processed to remove signal drift and suppress noise. Each time series will first be inspected for gross artifacts or motion, and if such artifacts or motions are evident, they will be removed from further analysis. The data will otherwise be realigned to compensate for motion artifact. The images will then be put into Talairach space by a non-linear spatial normalization of the data to remove the signal drift. A Gaussian filter with full width at one-tenth maximum equal to two to three times the acquired resolution but less than 10 mm will be applied. The fMRI design matrix is specified and estimated using the general linear model. This includes correction for temporal autocorrelation to attenuate high frequency components. To control for large vessel effects and other artifact, voxels where the standard deviation is more that 5% of the mean intensity will be eliminated from the functional image series for each run before further analysis. For each subject, the differences in MRI signal between the on and off epochs will be calculated on a voxelwise basis for each activation cycle. This will demonstrate the mean difference in signal change between the auditory task and the control condition, and t-maps will be generated displaying the significance of these differences, which are then transformed to a z distribution, which reflects differences between two conditions at each voxel. To minimize false positive and false negative results, two different statistical analyses will be performed: a fixed effect design and a more stringent conjunction analysis. For conjunction analysis, individual voxels will be significantly activated only if each subject activates the identical voxel at or above a height threshold of p<0.05 (corrected), voxels not activated in every subject will be eliminated.

Based on these tests and analyses, the location for implanting the electrode array on the brain is determined. The surgical implantation of the electrode array and its associated pulse generator is indicated at 18 in FIG. 1. Implantation involves the placement of an electrode array typically having four to eight electrodes arranged in a rectangular configuration into the brain. In the preferred embodiment of the invention the electrode array implanted is Medtronic, Inc. model 3387IES. The electrode is implanted into the active regions within Heschyl's gyrus using MEG guided neuronavigation. The exact placement of the electrodes will be determined by the localization provided by the MEG and fMRI studies described above.

Once the electrode is properly placed and the region tested for responsiveness to stimulation, the dura will be closed and an electrode cable secured to it. The cable will then exist through the temporalis muscle and fascia, where it will be secured with a closing suture. An extension cable will be attached to the primary electrode cable and secured.

A programmable pulse generator of the type manufactured by Advanced Neuromodulation Systems or Medtronic, Inc. will be implanted into either the flank or chest areas.

At some time after the implantation, at least one week, and at intervals thereafter, the stimulation pattern generated by the pulse generator for the electrode array is evaluated in terms of its effect in modifying the tinnitus. The generator may be adjusted in terms of frequency, pulse width, intensity, time on and time off. A particular pattern is chosen and the patient's perceived reduction in the tinnitus is determined. If there is no perceived reduction then the parameters will be varied. The pulse width preferably may be varied from 60-450 ms and the frequency can be varied from 2-185 Hz. Amplitude can be varied from 0 v to 10.5 v. Stimulus pattern combinations may also be varied in terms of the polarity of signals applied to the various electrodes of the array.

A patient will typically notice the effect of a particular pattern within 20 seconds and the parameters varied until the maximum relief is provided to the patient.

Once the amplitude, pulse width and frequency are optimized to the patient, the electrode configuration will be changed to drive the current to the most active site in the cortex; the site that was most suspicious as the tinnitus generator. The stimulated parameters, or at least amplitude and pulse width, will need to be readjusted for each electrode configuration.

The pulse generator may preferably be programmed so as to provide an elongated train of pulses with the amplitudes of the pulses, the pulse widths, and the timing between the pulses, possibly the frequency of the pulses, varied over a sufficient period of time that the brain perceives a pattern as random and continuously varying. The brain will thus avoid acclimation to a particular pattern which may lead to the resumption of the tinnitus.

Alternatively, the pulse generator could be equipped with a random number generator which continuously varies the controllable parameters of the pulse train in an indeterminate manner.

Having thus described my invention, I claim:

1. In a method of treatment of a patient for tinnitus, comprising implanting an array of electrodes in an area of the patient's brain believed to be a single site of the tinnitus, connecting a pulse generator, programmable as to output pulse pattern, to the electrodes of the array, the pulse generator being controllable as to pulse width, voltage and timing, causing the pulse generator to generate a time varying output pulse pattern of electrical impulses to the patient's brain through the array of electrodes, and varying the time varying output pulse pattern of the generator to change the time varying output pulse pattern based on an effect of the time varying pulse pattern based on an effect of the output pulse pattern on the tinnitus, an improved method of determining a precise area of the patient's brain believed to be a single site of the tinnitus, comprising:

determining a nature of the patient's tinnitus by presenting the patient with a plurality of tones of varying amplitude at each of a plurality of frequencies and obtaining the patient's subjective determination as to which amplitude matches perceived tinnitus and then presenting the patient with a series of two tones at separated frequencies and said determined matching amplitude using a two-alternating forced choice procedure to determine sound amplitudes and pitches that most closely simulate the patient's tinnitus;

generating audio tones based on said determination of sound amplitudes and pitches that most closely simulate the patient's tinnitus;

conducting brain imaging during generation of the audio tones based on said determination of sound amplitudes and pitches that most closely simulate the patient's tinnitus; and evaluating results of the brain imaging to determine the precise area of the patient's brain which appears to be a single site of the tinnitus.

2. The method of claim 1 in which the time varying output pulse pattern of the generator constitutes a train of pulses of varying widths at varying intervals to prevent acclimation of the brain to the pulse pattern.

3. The method of claim 1 in which the time varying pulse pattern is determined by evaluating the effectiveness of a particular pattern on a patient's tinnitus.

4. The method of claim 1 wherein the brain imaging includes functional magnetic resonance imaging.

5. The method of claim 1 wherein the brain imaging includes magnetoencephalography.

6. The method of claim 1 wherein the brain imaging includes both functional magnetic resonance imaging and magnetoencephalography.

* * * * *

UNITED STATES PATENT AND TRADEMARK OFFICE
CERTIFICATE OF CORRECTION

| | | |
|---|---|---|
| PATENT NO. | : 8,014,870 B2 | Page 1 of 1 |
| APPLICATION NO. | : 11/201454 | |
| DATED | : September 6, 2011 | |
| INVENTOR(S) | : Michael D. Seidman | |

It is certified that error appears in the above-identified patent and that said Letters Patent is hereby corrected as shown below:

Column 10, Lines 19-20 - insert --output-- after "varying"
Column 10, Line 20 - delete "based on an effect of the output pulse pattern"

Signed and Sealed this
Twenty-fourth Day of April, 2012

David J. Kappos
*Director of the United States Patent and Trademark Office*